United States Patent [19]
Kawata et al.

[11] Patent Number: 5,616,768
[45] Date of Patent: Apr. 1, 1997

[54] PROCESS FOR PURIFYING PHOSPHORIC ESTERS

[75] Inventors: Shigeru Kawata, Osaka; Kazuo Noguchi, Aichi; Kenji Ako, Nara; Shin Nakamura, Aichi, all of Japan

[73] Assignee: Daihachi Chemical Industry Co., Ltd., Osaka, Japan

[21] Appl. No.: 491,402

[22] Filed: Jun. 19, 1995

[30]   Foreign Application Priority Data

Jun. 23, 1994 [JP] Japan .................................. 6-142023

[51] Int. Cl.$^6$ ...................................................... C07F 9/02
[52] U.S. Cl. ............................................ 558/146; 558/147
[58] Field of Search ...................................... 558/146, 147

[56]       References Cited

U.S. PATENT DOCUMENTS 3,959,414   5/1976   Shim et al. ............................. 260/928

FOREIGN PATENT DOCUMENTS 0509506    10/1992   European Pat. Off. .
63-227632   9/1988   Japan .
152379      2/1989   Japan .

OTHER PUBLICATIONS

Gustav Jacobsen, Ber. 8, 1519 (1875).
M. Rapp, Ann. 224, 156 (1875).
English Language Abstract of Japanese Application No. 1–52379 of Feb. 28, 1989.
English Language Abstract of Japanese Application No. 63–227632 of Sep. 21, 1988.
Database WPI, Section Ch, Week 8650, Derwent Publications Ltd., London, abstract of JP 61246147, 1986.
Chemical Abstracts, vol. 083, No. 19, Nov. 10, 1975, Columbus, Ohio, US; Abstract No. 163759, Dul M et al.

*Primary Examiner*—Johann Richter
*Assistant Examiner*—Laura R. Cross
*Attorney, Agent, or Firm*—Greenblum & Bernstein P.L.C.

[57]       ABSTRACT

A process for purifying a phosphoric ester, which comprises treating a crude phosphoric ester with an epoxy compound, heating the resultant in the presence of water, washing the resultant with water, and removing the residual water. The obtained phosphoric esters have low acid value and are excellent in physical properties such as heat resistance, resistance to hydrolysis and storage stability, and are useful as plasticizers and/or flame-retardants.

12 Claims, No Drawings

PROCESS FOR PURIFYING PHOSPHORIC ESTERS

BACKGROUND OF THE INVENTION.

1. Field of the Invention

The present invention relates to a process for purifying phosphoric esters, and particularly to a purification method for preparing phosphoric esters which have low acid value and are excellent in physical properties such as heat resistance, storage stability and resistance to hydrolysis.

2. Description of the Prior Art

Known methods of synthesizing phosphoric esters include a method by dehydrochlorination of phosphorous oxychloride with alcohols or phenols. With such synthetic methods, however, complete esterification cannot be attained with the resulting that the synthesized phosphoric esters show some acid values resulting from the phosphoric acid or its chloride which is as the starting material.

Therefore, in general, in order to obtain the phosphoric esters having low acid values, neutralization with basic substances including wet neutralization with an alkaline metal hydroxide such as sodium hydroxide and dry neutralization with an alkaline metal compound such as calcium carbonate and magnesium hydroxide is conducted, followed by washing with water and distilling to purify the phosphoric esters.

However, where phosphoric esters having a high viscosity are purified by the wet neutralization with alkaline metal hydroxide, due to the difficulty in separation of aqueous layer and oily layer, the treating time is long and a slight amount (e.g., several to hundreds of ppm) of the alkaline metal remains in the oily layer after the separation. The alkaline metal remaining in the purification process of the phosphoric esters disadvantageously lowers heat resistance and resistance to hydrolysis of the phosphoric esters.

Various attempts have been made to decrease the remaining amount of the alkaline metal. These attempts include diluting the phosphoric esters with an organic solvent to lower the viscosity and salting-out to readily separate the aqueous layer from the oily layer. Those attempts, nevertheless, fail to prevent the slight amount of the alkaline metal from being present in the product layer. For this reason, the phosphoric esters are washed many times with water to remove the alkaline metal. The same problem applies to the dry neutralization.

Also, the wet neutralization with alkaline metal hydroxide is not applicable to some of the phosphoric esters, leading to emulsification of the whole solution of the phosphoric esters and insufficient separation of the aqueous layer from the oily layer.

The phosphoric esters can also be purified by distillation, and such a purification technique by distillation is applicable to the phosphoric esters having low molecular weight without the problem of alkaline metal remaining in the oily layer. With this technique, however, distillation apparatus are required such as fractionating apparatus having a good fractional distillation effect to remove impurities other than the alkaline metal which may reduce the physical properties (e.g., heat resistance, storage stability and resistance to hydrolysis) of the phosphoric esters, and increasing the molecular weight of the phosphoric esters makes it difficult to purify the phosphoric esters by distillation. In addition, the low yield with the purification technique leads to higher cost of the phosphoric esters to be obtained.

In addition to the remaining alkaline metal in the purification process, the impurities causing the lowering of the heat resistance and resistance to hydrolysis of the phosphoric esters include compounds not completely esterified such as compounds having the phosphoric acid or alcohols bonded to catalysts, and other impurities in a slight amount. Those impurities cannot be completely removed by the above described purification technique such as neutralization and distillation. The purification technique can produce the phosphoric esters having low acid value but not the phosphoric esters excellent in heat resistance, resistance to hydrolysis, storage stability or the like.

Japanese Patent Publication No. Hei 1-52379 describes a purification method of a dialkyl maleate, comprising the steps of neutralizing an acid component in a reaction solution containing the dialkyl maleate obtained by reacting maleic acid with an alcohol, with a basic substance such as sodium hydroxide and potassium hydroxide; heating the resultant at an elevated temperature; and reneutralizing with the basic substance an acid component generated by the heat treatment; and distilling the resultant.

According to the description of the publication, the method is characterized in that a purification technique by distillation becomes available by decomposing the impurities into the acid components using heat treatment and then by reneutralizing the resultant.

In purifying the phosphoric esters in accordance with this method, however, the basic substance remains in the ester prior to distillation because of the neutralization process included in the method, making it impossible to employ the method for the ester easily to be emulsified as described above. In addition, a problem with this method is that the impurities cannot be removed, without distillation.

SUMMARY OF THE INVENTION

The present invention has been conceived in view of the above problems, and an object of the invention is to provide a process for purifying a phosphoric ester which gives a phosphoric ester which has low acid value and is excellent in heat resistance, resistance to hydrolysis and storage stability, wherein neither a neutralization process with alkaline metal compound nor a distillation process for removal of impurities is required.

In other words, the present invention provides a process for purifying phosphoric ester, which comprises treating a crude phosphoric ester with an epoxy compound; heating the resultant in the presence of water; washing the resultant with water; and removing the residual water.

PREFERRED EMBODIMENTS OF THE INVENTION

The phosphoric esters to be treated by the method of the present invention are usually those known in the art as plasticizers and/or flame-retardants of resins, although they are not particularly limited to them as far as they contain impurities derived from their synthetic method.

Typically, the phosphoric esters can be represented by the following formula:

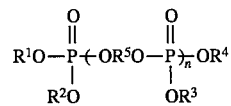

in which $R^1$, $R^2$, $R^3$ and $R^4$ are, the same or different, an aliphatic hydrocarbon group, preferably an alkyl group having 8 to 18 carbon atoms provided that n=0, or an aromatic hydrocarbon group, preferably an aryl group having 6 to 15 carbon atoms provided that n=0 to 30; $R^5$ is a bivalent organic group optionally having two hydroxy groups, preferably arylene group optionally having two hydroxy groups; and n is an integer of 0 to 30.

Examples of the alkyl groups include 2-ethylhexyl, n-octyl, sec-octyl, nonyl, decyl, dodecyl, palmityl and stearyl.

Examples of the aryl groups include phenyl, cresyl, xylyl, 2,6-dimethylphenyl, 2,4,6-trimethylphenyl, butylphenyl and nonylphenyl.

Examples of the arylene groups include phenylenes and p,p'-(isopropylidene)diphenylene. The phosphoric esters of the present invention include monomers, dimers and trimers of the phosphoric esters. They can be used either singly or as a mixture thereof.

The crude phosphoric esters of the present invention contain impurities [e.g., alkaline metals used as reaction catalysts, compounds not completely esterified, compounds with metals (existing in the reaction catalyst) attached to a bond of the phosphoric esters, dimers formed with phosphoric diesters bonded thereto through metals in the reaction catalyst, and compounds formed with phosphoric acid or alcohols as starting materials bonded to the reaction catalyst] resulting from a synthetic method of the phosphoric esters. The purification method of the present invention is useful in preparing highly purified phosphoric esters, for example monomers, dimers, trimers etc. It is understood that hereinafter those impurities are included in the term impurities.

The phosphoric esters to be purified be the method of the present invention can be obtained by conventional methods known in the art. Generally, phosphorus oxychloride is reacted with an appropriate alcohol or phenol in the presence or absence of a catalyst such as Lewis catalyst (e.g., aluminum chloride, magnesium chloride or titanium tetrachloride). Specifically, phosphoric triesters can be prepared by reacting phosphorus oxychloride with a phenol in the presence of Lewis catalyst (see e.g., G. Jacobsen, Ber. 8, 1519 (1875); M. Rapp, Ann. 224, 156 (1884)). Aromatic bisphosphate can be obtained by reacting phosphorus oxychloride with an aromatic monohydroxy compound (monovalent phenol) in the presence of Lewis catalyst, followed by reacting the resulting diarylphospho halidate with an aromatic dihydroxy compound (bivalent phenol) in the presence of the same catalyst (see, e.g., EP92106623.9). Also, Japanese Unexamined Patent Publication No. Sho 63 (1988)-227632 describes that phosphorus oxychloride is reacted with an aromatic dihydroxy compound and the resulting mixture on which unreacted phosphorus oxychloride is removed is reacted with an aromatic monohydroxy compound to obtain an aromatic diphosphate. Alternatively, an aromatic diphosphate may be obtained by reacting phosphorus oxychloride with a mixture of monohydroxy compound and dihydroxy compound.

Preferred examples of the alcohols used in the method for preparing the crude phosphoric esters include aliphatic alcohols such as octyl alcohol, 2-ethylhexyl alcohol, capryl alcohol, nonyl alcohol, n-decyl alcohol, lauryl alcohol, tridecyl alcohol, cetyl alcohol and stearyl alcohol; alicyclic alcohols such as cyclohexanol; and aromatic alcohols such as benzyl alcohols.

Preferred examples of the phenols used in the method for preparing the crude phosphoric esters include phenol, cresol, xylenol, resorcin, hydroquinone, bisphenol A, bis-phenol F, bisphenol S, biphenol, naphthol.

In the method for preparing the crude phosphoric esters, the reaction conditions such as the amount of reaction catalyst to be used, reaction ratio of phosphoric acid relative to the alcohol or the phenol, reaction ratio of phosphorus oxychloride relative to the alcohol or the phenol, reaction temperature and reaction time are properly determined within the knowns scope.

The phosphoric esters thus prepared usually contain a large amount of the impurities as described above, and the purification method of the present invention provides highly purified phosphoric esters by removing the impurities from the crude phosphoric esters that contain a large amount of the impurities.

The purification method of the present invention will now be detailed hereinbelow.

The crude phosphoric esters used in the purification method of the present invention are either in a solid form or in a liquid form. The purification method of the present invention can be used for the crude phosphoric esters in both forms, but preferably in a liquid form.

In the case of the crude phosphoric esters in a solid form, they are preferably used by being dissolved in a solvent. The solvent used to dissolve the crude phosphoric esters can be any solvents that can dissolve the crude phosphoric esters and do not inhibit the effect of the epoxy compounds as expected below. Particular examples of the solvents include an aromatic solvent such as toluene, xylene and dichlorobenzene; an aliphatic solvent such as hexane and heptane; an alicyclic solvent such as cyclohexane. Among those, preferred is the aromatic solvent because of its good solubility to the crude phosphoric esters. The present invention, however, cannot employ as the solvent for dissolving the crude phosphoric esters an alcoholic compound having a hydroxyl group or a compound having an amino group, because it is disadvantageous that those compounds cause ester interchange with the phosphoric esters to be purified to lower their purity or that they are reacted with the impurities to form salts or may be reacted with the epoxy compounds.

The purification method of the present invention starts with treating the crude phosphoric ester with the epoxy compound. This treatment is conducted in order to mask with an epoxy group an acid component of the impurities contained in the crude phosphoric ester.

The term "epoxy compound" used in the present invention means aliphatic, aromatic, alicyclic, and heterocyclic compounds.

In particular, preferred examples of the aliphatic epoxy compounds include ethylene oxide, propylene oxide, butylene oxide, 3,4-epoxybutanol, polyethylene glycol(200) diglycidyl ether, polyethylene glycol(400) diglycidyl ether, sorbitol polyglycidyl ether, sorbitan polyglycidyl ether, polyglycerol polyglycidyl ether, pentaerythritol polyglycidyl ether, diglycerol polyglycidyl ether, glycerol polyglycidyl cidyl ether, trimethylolpropane polyglycidyl ether, propylene glycol diglycidyl ether, polytetramethylene glycol diglycidyl ether, allylglycidyl ether, 2-ethylhexyl glycidyl ether, diglycidyl adipate and dibromoneopentyl glycol diglycidyl ether.

Preferred examples of the alicyclic epoxy compounds include 1-methyl-1,4-epoxycycloheptane, 2,3-epoxycyclopentanone, 3,4-epoxycycloocten, 2,3-epoxynorbornane, 2-(3,4-epoxycyclohexyl) -1,3-dioxolan, 4,5-epoxy-1-p-menthene, 1,2-epoxy -4-p-menthene, 1-(glycidyloxymethyl)-3,4-epoxycyclohexane 2,3-epoxy-3,5,5-trimethylcyclohexanone and bis(2,3-epoxycyclopentyl)ether.

Preferred examples of the aromatic, heterocyclic and other epoxy compounds include phenylglycidyl ether, p-tertbutylphenylglycidyl ether, triglycidyl tris(2-hydroxyethyl-)isocyanurate, o-phthalic acid diglycidyl ether, hydroquinone diglycidyl ether, terephthalic acid diglycidyl ether, glycidyl phthalimide, dibromophenylglycidyl ether, bisphenol A diglycidyl ether, bisphenol S diglycidyl ether, bisphenol F diglycidyl ether and additional reaction products thereof.

The present invention can use any epoxy compounds as described above, but in operational and economical scales preferably uses the epoxy compounds in a gas form or in a liquid form at room temperature. Examples of the epoxy compounds to be used in the gas form or in the liquid form at room temperature include ethylene oxide, propylene oxide and butylene oxide.

The molecular weight of the epoxy compounds used in the present invention is preferably about 40 to about 1000, more preferably about 40 to about 500, because the use of the epoxy compounds having too high molecular weight results in prolonged reaction time. In use of such epoxy compounds having high molecular weight, raising the reaction temperature enables the reaction time to be shortened.

The method for treating the crude phosphoric ester with the epoxy compound is not particularly limited, and properly determined depending upon the physical properties, reactivity or other conditions of the epoxy compound used. When the crude phosphoric ester is treated with, for example, ethylene oxide in a gas form, the treatment can be conducted by blowing ethylene oxide in the gas form through an insertion duct into the crude phosphoric ester. When the crude phosphoric ester is treated with propylene oxide in a liquid form, the treatment can be conducted by adding propylene oxide dropwise to the crude phosphoric ester or adding propylene oxide to the crude phosphoric ester followed by heating the mixture.

The temperature at which the crude phosphoric ester is treated with the epoxy compound is properly determined depending on the type of epoxy compound used. In use of ethylene oxide and propylene oxide for example, the temperature is preferably about 50° C. to about 200° C., and more preferably about 80° C. to 160° C., taking the reactivity of the epoxy compound and loss caused by scattering into consideration. That is because at a temperature lower than 50° C. the reaction time is prolonged because the reactivity of the epoxy compound is low and the impurities cannot be thoroughly removed by an operation conducted after the crude phosphoric ester is treated with the epoxy compound because the reaction is not sufficiently performed. On the other hand, at a temperature higher than 200° C., propylene oxide that has a high volatility volatilizes and flows out of the system prior to the reaction, making it necessary to excessively increase the amount of the epoxy compound used, and the impurities cannot be thoroughly removed by an operation conducted after the crude phosphoric ester is treated with the epoxy compound with the same reason as described above that the reaction is not sufficiently performed due to the flowing-out of the epoxy compound, thereby further bringing about air pollution from rolatilization of propylene oxide.

The time required for treating the crude phosphoric ester with the epoxy compound is properly determined depending on the sort and molecular weight of the epoxy compounds to be used and the reaction time. In general, the time is preferably about 0.5 to 1 hour, for example about 0.5 hour for propylene oxide having molecular weight of about 58, and about 1 hour for bisphenol A diglycidyl ether having molecular weight of about 340.

In treating the crude phosphoric ester with the epoxy compound, for the amount of the epoxy compound to be added to the crude phosphoric ester, the corresponding amount to the acid value of the crude phosphoric ester is sufficient, but it is preferred to add the epoxy compound at a slightly greater amount than the corresponding amount to the acid value of the phosphoric ester, taking the reactivity of the epoxy compound and loss caused by scattering when the epoxy compound having a low boiling point are used into consideration. In general, the preferred ratio of the crude phosphoric ester relative to the epoxy compound to be added thereto is about 1:1 to about 1:20 (molar ratio), based on the acid value of the crude phosphoric ester.

In the purification method of the present invention, it has not been confirmed what reaction is caused by treating the crude phosphoric ester with the epoxy compound, but the following reaction is presumed to be caused. That is, it is considered that treating the crude phosphoric ester with the epoxy compound allows an acid component existing in the impurities contained in the crude phosphoric ester to be masked with an epoxy group, seemingly lowering the acid value of the phosphoric ester as in the case of neutralization. In particular, in the compound that among impurities, has the metal attached thereto, the treatment allows the metal to be substituted by the epoxy group, and the substituted part is hydrolyzed in the following heat treatment, thereby transforming the compound into water-soluble compound.

In the compound not completely esterified, to the acid component thereof is attached the epoxy group, and in some cases the part to which the epoxy group is attached is hydrolyzed in the following heat treatment. In view of the stereostructure, however, it is considered that a site thermally unstable that is not the part to which the epoxy group is attached is subjected to hydrolysis, whereby the compound not completely esterified is transformed into the compound having low molecular weight and highly water-soluble.

After being treated with the epoxy compound as described above, the crude phosphoric ester is heated in the presence of water, but prior to the heat treatment it is preferred to wash the epoxy treated liquid with water, i.e., after the crude phosphoric ester was treated with the epoxy compound. That is because by washing the treated liquid with water, the water-soluble impurities (e.g., esterification reaction catalysts (metals) remaining in the crude phosphoric esters, and unreacted epoxy compounds) can be removed at that stage.

One water washing would usually be sufficient. Suitably, water used in washing is in a proportion of about 10–100% by weight relative to the total amount of the reaction mixture. Particular washing operations include an operation comprising adding water to the treated liquid after the crude phosphoric ester was treated with the epoxy compound; stirring the mixture; allowing the mixture to stand to separate the aqueous layer from the oily layer; and removing the overlaying aqueous layer using a separating funnel or the like.

Thus, when the treated liquid, after the crude phosphoric ester was treated with the epoxy compound, is washed with water prior to the heat treatment, several % of water remains in the oily layer, irrespective of the presence or absence of a solvent. Since this water allows the impurities remaining after heat treatment to be removed by hydrolysis, no water is further required to be added in the following heat treatment, Without mentioning, even lacking the washing operation, the purification method of the present invention allows satisfactory purification of the phosphoric esters.

After being treated with the epoxy compound, the crude phosphoric ester is preferably washed, and then heated in the presence of water.

The heat treatment in the present invention is intended to hydrolyze the impurities that are thermally unstable, and conducted under conditions sufficiently controlled so that the phosphoric ester to be purified is not subjected to the hydrolysis by the heat treatment.

In other words, the presence of water is essential to the heat treatment in hydrolyzing the impurities that are thermally unstable to transform them into the water-soluble components. The impurities thus transformed into the water-soluble components by the heat treatment can be removed in the following washing process. Therefore, after treating the crude phosphoric ester with the epoxy compound, it is necessary when the washing is not conducted, to add water to the treated liquid. The amount of water to be added in the heat treatment is not particularly limited.

It is essential that the heat treatment temperature should be a temperature at which the phosphoric ester to be purified is not hydrolyzed, and the temperature is properly determined depending upon the sort of the phosphoric esters to be purified. In general, it is suitably about 100° C. to about 200° C., and preferably about 100° C. to 160° C., because at a temperature lower than 100° C., the time required for the hydrolysis of the impurities is prolonged, which is disadvantageous in economical scale and because at a temperature higher than 200° C., there is a possibility of the phosphoric ester to be purified being hydrolyzed and also the impurities are not sufficiently hydrolyzed due to quick evaporation of water existing in the reaction system, whereby the impurities unfavorably affecting the physical properties of the phosphoric ester are not thoroughly removed. At a temperature within the above-defined scope, the impurities can efficiently be hydrolyzed by water introduced into the reaction system, without hydrolyzing the phosphoric ester.

The time required for the heat treatment is suitably about 0.5 to 2 hours, and properly determined depending upon the heat treatment temperature. At a high temperature, the heat treatment can be completed in a shorter time.

For heat treatment methods, methods generally used in the art can be employed, and preferably employed is steam distillation. The advantages of such steam distillation are that introducing heated steam into the reaction system permits water supply and heat treatment, and that compounds having a low boiling point can simultaneously be removed.

In the present invention, this heat treatment allows hydrolysis to start at a part thermally unstable in the impurities, transforming the impurities into the water-soluble substances.

After the heat treatment, the impurities that are hydrolyzed and transformed into the water-soluble compounds are removed with washing. Particular washing operations are performed in the same manner as described above. It is sufficient to wash once. Suitably, water used in washing is in a proportion of about 10 to 100% by weight relative to the total amount of the reaction mixture. With this washing process, all the water-soluble impurities that affect heat resistance, resistance to hydrolysis and storage stability are finally removed.

By removing residual water after washing, a purified phosphoric ester can be prepared. The methods for removing water include methods generally used in the art, and preferably employed is distillation conducted under reduced pressure, preferably at about 100° C. to about 150° C.

In use of the crude phosphoric esters in a solid form, the solvents used to dissolve them can simultaneously in some cases be removed by distilling under reduced pressure as described above, but it is preferable to conduct steam distillation after dehydration and drying.

Further, preferably, steam distillation is conducted after removal of water in order to remove the impurities (e.g., phenols which are starting materials in synthesis of the crude phosphoric esters) having a low boiling point and difficult to dissolve in water.

The phosphoric esters thus purified contain a small amount of the impurities, have low acid value and are excellent in the physical properties such as heat resistance, storage stability and resistance to hydrolysis.

Therefore, the phosphoric esters purified by the method of the present invention are advantageous in having low acid value, thereby reducing corrosion of metal molds in the process of molding the resins when used as plasticizers or flame-retardants of resins, and being advantageous in having excellent heat resistance, thereby showing no changes in composition at molding temperature. Accordingly, the phosphoric esters prepared by the method of the present invention are suitable for use in plasticizers or flame retardants of resins.

The present invention is further described by way of the following Synthesis Examples and Working Examples, whose purpose is merely indicative but not limitative of the scope of the invention itself.

In the following Examples, heat resistance test was performed in such a manner that samples were injected into test tubes, which were not sealed, and heated for 3 hours in an electric oven set to 250° C. to observe their acid values and changes in composition. Note that compounds E and F, the flash points of which are low, were heated for 1 hour in an electric oven set to 200° C. to observe their acid values and changes in composition in the same manner.

SYNTHESIS EXAMPLE 1

[Synthesis of Compound A (Crude Phosphoric Ester Compound)]

Phosphorus oxychloride (307 g) was reacted with cresol (432 g) in the presence of aluminum chloride catalyst under ordinary pressure, to which bisphenol A (228 g) was added. The reaction was continued until hydrochloric acid was generated in a theoretical amount under reduced pressure. After the reaction mixture was washed with an aqueous solution of hydrochloric acid to remove the catalyst, water was distilled off under reduced pressure to obtain a compound A (740 g) which was a colorless viscous liquid having a main component of 2,2-bis{4-[bis(methylphenoxy)phosphoryl]oxyphenyl}propane with an acid value of 1.5.

SYNTHESIS EXAMPLE 2

[Synthesis of Compound B (crude Phosphoric Ester Compound)]

Phosphorus oxychloride (307 g) was reated with phenol (376 g) in the presence of magnesium chloride catalyst under ordinary pressure, to which bisphenol A (228 g) was added. The reaction was continued until hydrochloric acid was generated in a theoretical amount under reduced pressure. After the reaction mixture was washed with an aqueous solution of oxalic acid to remove the catalyst, water was distilled off under reduced pressure to a obtain compound B (690 g) which was a colorless viscous liqid having a main component of 2,2-bis{4-[bis(phenoxy)phosphoryl]oxyphenyl}propane with an acid value of 1.3.

SYNTHESIS EXAMPLE 3

[Synthesis of Compound C (Crude Phosphoric Ester Compound)]

Phosphorus oxychloride (307 g) was reacted with phenol (376 g) in the presence of magnesium chloride catalyst under ordinary pressure, to which resorcin (110 g) was added. The reaction was continued until hydrochloric acid was generated in a theoretical amount under reduced pressure. After the reaction mixture was washed with an aqueous solution of oxalic acids to remove the catalyst, water was distilled off under reduced pressure to obtain a compound C (570 g) which was a colorless viscous liquid having a main component of m-phenylenebis(diphenylphosphate) with an acid value of 0.6.

SYNTHESIS EXAMPLE 4

[Synthesis of Compound C (Crude Phosphoric Ester Compound)]

Phosphorus oxychloride (307 g) was reacted with phenol (376 g) in the presence of magnesium chloride catalyst under ordinary pressure, to which resorcin (220 g) was added. The reaction was continued until hydrochloric acid was generated in a theoretical amount under reduced pressure. After the reaction mixture was washed with an aqueous solution of hydrochloric acid to remove the catalyst, water was distilled off under reduced pressure to obtain a compound D (680 g) which was a pale yellow viscous liquid having a main component of m-hydroxyphenyldiphenylphosphate with an acid value of 0.8.

SYNTHESIS EXAMPLE 5

[Synthesis of Compound E (Crude Phosphoric Ester Compound)]

Phosphorus oxychloride (307 g) was reacted with 2-ethylhexanol (780 g) in the presence of magnesium chloride catalyst under ordinary pressure. After the reaction mixture was washed with an aqueous solution of hydrochloric acids to remove the catalyst, water was distilled off under reduced pressure to obtain compound E (863 g) which was a liquid of tri-2-ethylhexylphosphate with an acid value of 0.8, a boiling point of 220° to 250° C./5mmHg and a flash point of 204° C.

SYNTHESIS EXAMPLE 6

[Synthesis of Compound F (Crude Phosphoric Ester Compound)]

Phosphorus oxychloride (307 g) was reacted with phenol (564 g) in the presence of magnesium chloride catalyst under ordinary pressure. The reactant was heated to 140° C. under reduced pressure to continue the reaction until no hydrochloric acid was generated. After the reaction mixture was washed with an aqueous solution of hydrochoric acid to remove the catalyst, water was distilled off under reduced pressure to remove water to obtain a compound F (650 g) which was a white solid of triphenyl phosphate with an acid value of 1.1, a boiling point of 260° C./20mmHg and a flash point of 225° C.

WORKING EXAMPLE 1

To the compound A (740 g) was added propylene oxide (7.1 g) and the mixture was reacted at 80° C. for 2 hours. After washing with water (400 g), the resultant was heated at 140° C. for 0.5 hours and washed with water (400 g) again. Water was distilled off under reduced pressure to obtain a purified product A which was a colorless viscous liquid with an acid value of 0.08.

The reaction condition in the purification process of the compound A is shown in Table 1.

The physical properties of the purified product thus prepared were measured. The acid value given after the purified product A was steam-distilled for 4 hours was 0.09 while that given after a heat test was performed at 250° C. for 3 hours was 0.69. The molecular weight distribution measured by means of gel permeation chromatography indicated no changes occurred in composition before and after the heat test.

The results of the physical properties are shown in Table 2.

WORKING EXAMPLE 2

The same operation was performed as in Working Example 1, except that the reaction temperature of propylene oxide in Working Example 1 was changed to 100° C. The reaction condition in the purification process of the compound A is shown in Table 1. The physical properties of the purified product A were measured and the results are shown in Table 2.

WORKING EXAMPLE 3

The same operation was performed as in Working Example 1, except that the reaction temperature of propylene oxide in Working Example 1 was changed to 120° C. The reaction condition in the purification process of the compound A is shown in Table 1. The physical properties of the purified product A were measured and the results are shown in Table 2.

WORKING EXAMPLE 4

The same operation was performed as in Working Example 1, except that the reaction temperature of propylene oxide in Working Example 1 was changed to 160° C. The reaction condition in the purification process of the compound A is shown in Table 1. The physical properties of the purified product A were measured and the results are shown in Table 2.

WORKING EXAMPLES 5 to 7

The same operation was performed as in Working Example 1, except that the heating temperature in Working Example 1 was changed to 100° C. (Working Example 5), 120° C. (Working Example 6) and 160° C. (Working Example 7), respectively. The reaction condition in the purification process of the compound A is shown in Table 1. The physical properties of the purified product A were measured and the results are shown in Table 2.

WORKING EXAMPLE 8

The same operation was performed as in Working Example 1, except that propylene oxide in Working Example 1 was replaced by ethylene oxide. The purified product A thus obtained was a colorless viscous liquid with an acid value of 0.08. The acid value of the purified product was 0.09 after steam distillation for 4 hours and 0.71 after a heat test at 250° C. for 3 hours. The molecular weight distribution measured by means of gel permeation chromatography (GPC) indicated no changes occurred in composition before and after the heat test.

The reaction condition in the purification process of the compound A is shown in Table 1 and the physical properties of the purified product A are shown in Table 2.

WORKING EXAMPLE 9

The same operation was performed as in Working Example 1, except that propylene oxide in Working Example 1 was replaced by polyethylene glycol(400) diglycidyl ether. The purified product A thus obtained was a colorless viscous liquid with an acid value of 0.08. The acid value of the purified product A was 0.11 after steam distillation for 4 hours and 0.73 after a heat test at 250° C. for 3 hours. The molecular weight distribution measured by means of gel permeation chromatography (GPC) indicated no changes occurred in composition before and after the heat test.

The reaction condition in the purification process of the compound A is shown in Table 1 and the physical properties of the purified product A are shown in Table 2.

WORKING EXAMPLE 10

Propylene oxide (6.9 g) was added to the compound B (690 g) and the mixture was reacted at 120° C. for 1 hour. The reactant was washed with water (400 g) and heated at 140° C. for 0.5 hours. After the resultant was washed with water (400 g), water was distilled off under reduced pressure to obtain a purified product B which is a colorless viscous liquid with an acid value of 0.08.

The reaction condition in the purification process of the compound B is shown in Table 1.

The physical properties of the purified product thus obtained were measured. The acid value of the purified product B was 0.10 after steam distillation for 4 hours and 0.69 after a heat test at 250° C. for 3 hours. The molecular weight distribution measured by means of gel permeation chromatography indicated no change occurred in composition before and after the heat test.

The results of the physical properties of this purified product are shown in Table 2.

WORKING EXAMPLE 11

Propylene oxide (5.7 g) was added to the compound C (570 g) and the mixture was reacted at 120° C. for 1 hour. The reactant was washed with water (340 g) and heated at 140° C. for 0.5 hours. After the resultant was washed with water (340 g), water was distilled off under reduced pressure to obtain a purified product C which is a colorless viscous liquid with an acid value of 0.03.

The reaction condition in the purification process of the compound C is shown in Table 1.

The physical properties of the purified product thus obtained were measured. The acid value of the purified product C was 0.06 after steam distillation for 4 hours and 0.38 after a heat test at 250° C. for 3 hours. The molecular weight distribution measured by means of gel permeation chromatography indicated no change occurred in composition before and after the heat test.

The results of the physical properties of this product are shown in Table 2.

WORKING EXAMPLE 12

Propylene oxide (6.8 g) was added to the compound D (680 g) and the mixture was reacted at 120° C. for 1 hour. The reactant was washed with water (430 g) and heated at 140° C. for 0.5 hours. After the resultant was washed with water (430 g), water was distilled off under reduced pressure to obtain a purified product D which is a pale yellow viscous liquid with an acid value of 0.06.

The reaction condition in the purification process of the compound D is shown in Table 1.

The physical properties of the purified product thus obtained were measured. The acid value of the purified product D was 0.07 after steam distillation for 4 hours and 0.48 after a heat test at 250° C. for 3 hours. The molecular weight distribution measured by means of gel permeation chromatography (GPC) indicated no changes occurred in composition before and after the heat test.

The results of the physical properties of this product are shown in Table 2.

WORKING EXAMPLE 13

Ethylene oxide (4.3 g) was added to the compound E (863g) and the mixture was reacted at 110° C. for 0.5 hours. The reactant was washed with water (480 g) and heated at 120° C. for 0.5 hours. After the resultant was washed with water (480 g), water was distilled off under reduced pressure to obtain a purified product E which is a colorless liquid with an acid value of 0.01.

The reaction condition in the purification process of the compound E is shown in Table 1.

The physical properties of the purified product thus obtained were measured. The acid value of the purified product E was 0.05 after steam distillation for 4 hours and 0.38 after a heat test at 250° C. for 3 hours. The molecular weight distribution measured by means of gel permeation chromatography (GPC) indicated no changes occurred in composition before and after the heat test.

The results of the physical properties of this purified product are shown in Table 2.

WORKING EXAMPLE 14

The compound F (650 g) was dissolved in toluene (150 g), to which ethylene oxide (6.5 g) was added. The mixture was reacted at 110° C. for 0.5 hours. The reactant was washed with water (400 g) and heated at 140° C. for 0.5 hours. After the resultant was washed with water (400 g), water and toluene were distilled off under reduced pressure to obtain a purified product F which is a white solid with an acid value of 0.01.

The reaction condition in the purification process of the compound F is shown in Table 1.

The physical properties of the purified product thus obtained were measured. The. acid value of the purified product F was.0.18 after a heat test at 200° C. for 1 hour. The molecular weight distribution measured by means of gel permeation chromatography (GPC) indicated no changes occurred in composition before and after the heat test.

The results of the physical properties of this product are shown in Table 2.

COMPARATIVE EXAMPLE 1

The same operation was performed as in Working Example 1, except that the reaction temperature in Working Example 1 was changed to 50° C. The reaction condition in the purification process is shown in Table 1 and the results of the physical properties of the purified product are shown in Table 2.

COMPARATIVE EXAMPLE 2

The same operation was performed as in Working Example 3, except that the heat treatment in Working Example 3 was omitted. The acid value of the purified product thus obtained was 0.08 and was increased to 0.75 by subjecting the purified product to steam distillation. In addition, the acid value of the purified product was increased to 0.6 after stored at room temperature for 10 days, proving storage stability poor. The reaction condition in the purification process is shown in Table 1 and the results of the physical properties of the purified product are shown in Table 2.

COMPARATIVE EXAMPLE 3

The same operation was performed as in Working Example 3, except that the reaction temperature in Working Example 3 was changed to 80° C. The acid value of the purified product thus obtained was 0.07 and was increased to 0.67 by subjecting the purified product to steam distillation. In addition, the acid value of the purified product was increased to 0.5 after storage at room temperature for 10 days, indicating poor storage stability. The reaction condition in the purification process is shown in Table 1 and the results of the physical properties of the purified product are shown in Table 2.

COMPARATIVE EXAMPLE 4

Sodium carbonate (4 g) and water (400 g) were added to the compound A (740 g) and the mixture was neutralized at 80° C. for 1 hour. After separating water, the resultant was washed with the same amount of water 4 times to purify the compound A. The purified product has the acid value of 0.32 and sodium content of 52 ppm. A heat test was performed at 250° C. for 3 hours and the molecular weight distribution was measured by means of gel permeation chromatography (GPC), which indicated changes occurred in composition before and after the heat test. The reaction condition in the purification process is shown in Table 1 and the results of the physical properties of the purified product are shown in Table 2.

COMPARATIVE EXAMPLE 5

The same operation of Comparative Example 4 was performed, except that sodium carbonate in Comparative Example 4 was replaced by sodium hydroxide. The use of sodium hydroxide, however, caused emulsification in the mixture in the neutralization process, preventing the aqueous layer from being separated.

COMPARATIVE EXAMPLE 6

The same operation was performed as in Working Example 4, except that sodium carbonate in Comparative Example 4 was replaced by lithium hydroxide. Although no emulsification as in Comparative Example 5 occurred, the purified product thus obtained had the acid value of 0.09 and the lithium content of 21 ppm. A heat test was performed at 250° C. for 3 hours and the molecular weight distribution was measured by means of gel permeation chromatography (GPC), which indicated changes occurred in composition before and after the heat test. The reaction condition in the purification process is shown in Table 1 and the results of the physical properties of the purified product are shown in Table 2.

COMPARATIVE EXAMPLE 7

The same operation was performed as in Working Example 10, except that the heat treatment in Working Example 10 was omitted. The reaction condition in the purification process is shown in Table 1 and the results of the physical properties of the purified product are shown in Table 2.

COMPARATIVE EXAMPLE 8

The same operation was performed as in Working Example 11, except that the reaction temperature at which propylene oxide was reacted in Working Example 11 was changed to 60° C. and that the heating temperature was changed to 60° C. The reaction condition in the purification process is shown in Table 1 and the results of the physical properties of the purified product are shown in Table 2.

COMPARATIVE EXAMPLE 9

The same operation was performed as in Working Example 13, except that the reaction temperature at which ethylene oxide was reacted in working Example 11 was changed to 50° C. The reaction condition in the purification process is shown in Table 1 and the results of the physical properties of the purified product are shown in Table 2.

COMPARATIVE EXAMPLE 10

The same operation was performed as in Working Example 14, except that the heat treatment in Working Example 14 was omitted. The reaction condition in the purification process is shown in Table 1 and the results of the physical properties of the purified product are shown in Table 2.

TABLE 1

| | Crude product | | Treatment | | |
|---|---|---|---|---|---|
| No. | Sort | Acid value (AV) | Epoxy or neutralizing agent | Reaction temperature (°C.) | Heating temperature (°C.) |
| Work. Ex. 1 | A | 1.5 | propylene oxide | 80 | 140 |
| Work. Ex. 2 | A | 1.5 | propylene oxide | 100 | 140 |
| Work. Ex. 3 | A | 1.5 | propylene oxide | 120 | 140 |
| Work. Ex. 4 | A | 1.5 | propylene oxide | 160 | 140 |
| Work. Ex. 5 | A | 1.5 | propylene oxide | 120 | 100 |
| Work. Ex. 6 | A | 1.5 | propylene oxide | 120 | 120 |
| Work. Ex. 7 | A | 1.5 | propylene oxide | 120 | 160 |
| Work. Ex. 8 | A | 1.5 | ethylene oxide | 80 | 140 |
| Work. Ex. 9 | A | 1.5 | epoxy C (*) | 120 | 140 |
| Work. Ex. 10 | B | 1.3 | propylene oxide | 120 | 140 |

TABLE 1-continued

|  | Crude product | | Treatment | |
|---|---|---|---|---|
| No. | Sort | Acid value (AV) | Epoxy or neutralizing agent | Reaction temperature (°C.) | Heating temperature (°C.) |
| Work. Ex. 11 | C | 0.6 | propylene oxide | 120 | 140 |
| Work. Ex. 12 | D | 0.8 | propylene oxide | 120 | 140 |
| Work. Ex. 13 | E | 0.9 | ethylene oxide | 110 | 120 |
| Work. Ex. 14 | F | 1.1 | ethylene oxide | 110 | 140 |
| Comp. Ex. 1 | A | 1.5 | propylene oxide | 50 | 140 |
| Comp. Ex. 2 | A | 1.5 | propylene oxide | 120 | not heated |
| Comp. Ex. 3 | A | 1.5 | propylene oxide | 120 | 80 |
| Comp. Ex. 4 | A | 1.5 | sodium carbonate | — | — |
| Comp. Ex. 5 | A | 1.5 | sodium hydroxide | unseparatable | — |
| Comp. Ex. 6 | A | 1.5 | lithium hydroxide | — | — |
| Comp. Ex. 7 | B | 1.3 | propylene oxide | 120 | not heated |
| Comp. Ex. 8 | C | 0.6 | propylene oxide | 60 | 60 |
| Comp. Ex. 9 | E | 0.9 | ethylene oxide | 50 | 120 |
| Comp. Ex. 10 | F | 1.1 | ethylene oxide | 110 | not heated |

(*) ethlene glycol 400 diglycidyl ether

TABLE 2

| | properties of product | | | |
|---|---|---|---|---|
| | | Acid value | After heat test | |
| No. | Acid value (AV) | after steam distillation (AV) | Acid value (AV) | Change of GPC composition |
| Work. Ex. 1 | 0.08 | 0.09 | 0.69 | none |
| Work. Ex. 2 | 0.06 | 0.08 | 0.65 | none |
| Work. Ex. 3 | 0.07 | 0.08 | 0.68 | none |
| Work. Ex. 4 | 0.06 | 0.09 | 0.66 | none |
| Work. Ex. 5 | 0.06 | 0.09 | 0.69 | none |
| Work. Ex. 6 | 0.07 | 0.08 | 0.67 | none |
| Work. Ex. 7 | 0.05 | 0.07 | 0.72 | none |
| Work. Ex. 8 | 0.08 | 0.09 | 0.71 | none |
| Work. Ex. 9 | 0.08 | 0.11 | 0.73 | none |
| Work. Ex. 10 | 0.08 | 0.10 | 0.69 | none |
| Work. Ex. 11 | 0.03 | 0.06 | 0.38 | none |
| Work. Ex. 12 | 0.06 | 0.07 | 0.48 | none |
| Work. Ex. 13 | 0.01 | 0.05 | 0.38 | none |
| Work. Ex. 14 | 0.01 | — | 0.18 | none |
| Comp. Ex. 1 | 0.12 | 0.81 | 1.2 | present |
| Comp. Ex. 2 | 0.08 | 0.75 | 1.4 | present |
| Comp. Ex. 3 | 0.07 | 0.67 | 1.3 | present |
| Comp. Ex. 4 | 0.32 | 0.41 | 0.68 | present |
| Comp. Ex. 5 | — | — | — | — |
| Comp. Ex. 6 | 0.09 | 0.11 | 0.67 | present |
| Comp. Ex. 7 | 0.92 | 1.2 | 1.3 | present |
| Comp. Ex. 8 | 0.24 | 1.1 | 1.2 | present |
| Comp. Ex. 9 | 0.53 | 1.3 | 1.4 | present |
| Comp. Ex. 10 | 0.66 | 0.9 | 1.1 | present |

From the results shown in Table 2, it is apparent that the phosphoric esters purified by the method of the present invention have low acid value when compared to those prepared by the method of Comparative Examples (conventional purification method of phosphoric esters) and are excellent in heat resistance since no changes occurred in composition after the heat resistance test. Further, it is apparent that the phosphoric esters purified by the method of the present invention are excellent in storage stability since they have low increase ratio of the acid value after the heat test, compared to those purified by the method in Comparative Examples.

Thus, it is understood that the phosphoric esters purified by the method of the present invention are highly purified because of their excellent heat resistance and storage stability.

According to the purification method of the present invention, highly purified phosphoric esters can be provided which have low acid value and are excellent in physical properties such as heat resistance, resistance to hydrolysis and storage stability, since the impurities which affect the physical properties of the phosphoric esters such as heat resistance, resistance to hydrolysis and storage stability can be readily removed from the crude phosphoric esters without performing the neutralization with alkaline metal compound or distillation for removing the impurities.

Accordingly, the purification method of the present invention can also be applied to the phosphoric esters which cannot be neutralized or distilled. Further, the phosphoric esters purified by the method of the present invention are advantageous in having low acid value, thereby reducing corrosion of metal molds in the process of molding the resins when used as plasticizers or flame-retardants of resins, and being advantageous in having excellent heat resistance, thereby showing no changes in composition at molding temperature. Accordingly, the phosphoric esters prepared by the method of the present invention are suitable for use in plasticizers or flame-retardants of resins.

What we claimed is:

1. A process for purifying a phosphoric ester, which comprises treating a crude phosphoric ester with an epoxy compound, heating the resultant in the presence of water, washing the resultant with water, and removing the residual water.

2. A method according to claim 1, in which a mixture of the crude phosphoric ester treated with the epoxy compound is washed with water before heating the resultant.

3. A method according to claim 1, in which the epoxy compound has an molecular weight of 40 to 1,000.

4. A method according to claim 1, in which the epoxy compound is an aliphatic, aromatic, alicyclic or heterocyclic epoxy compound.

5. A method according to claim 4, in which the aliphatic epoxy compound is ethylene oxide, propylene oxide, butylene oxide, 3,4-epoxybutanol, polyethylene glycol(200) diglycidyl ether, polyethylene glycol(400) diglycidyl ether, sorbitol polyglycidyl ether, sorbitan polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, propylene glycol diglycidyl ether, polytetramethylene glycol diglycidyl ether, allylglycidyl ether, 2-ethylhexyl glycidyl ether, diglycidyl adipate or dibromoneopentyl glycol diglycidyl ether.

6. A method according to claim 4, in which the aliphatic epoxy compound is ethylene oxide, propylene oxide or butylene oxide.

7. A method according to claim 1, in which the molar ratio of the crude phosphoric ester and the epoxy compound is 1:1 to 1:20.

8. A method according to claim 1, in which the heating is conducted at about 80° C. to 200° C.

9. A method according to claim 1, in which the phosphoric ester is represented by the formula:

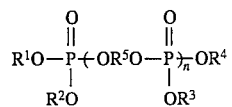

in which $R^1$, $R^2$, $R^3$ and $R^4$ are, the same or different, an aliphatic or aromatic hydrocarbon group provided that n=0, or an aromatic hydrocarbon group provided that n=1 to 30; $R^5$ is an arylene group; and n is an integer of 0 to 30.

10. A method according to claim 1, in which the aliphatic hydrocarbon group is an alkyl group having 8 to 18 carbon atoms.

11. A method according to claim 1, in which the aromatic hydrocarbon group is an aryl group having 6 to 15 carbon atoms.

12. A method according to claim 1, in which the arylene group is phenylene or p,p'-(isopropylidene)diphenylene.

* * * * *

UNITED STATES PATENT AND TRADEMARK OFFICE
CERTIFICATE OF CORRECTION

PATENT NO. : 5,616,768
DATED : April 1, 1997
INVENTOR(S) : S. KAWATA et al.

It is certified that error appears in the above-indentified patent and that said Letters Patent is hereby corrected as shown below:

At column 18, line 5 (claim 10, line 1), change "1 ," to ---9,---.

At column 18, line 8 (claim 11, line 1), change "1 ," to ---9,---.

At column 18, line 11 (claim 12, line 1), change "1 ," to ---9,---.

Signed and Sealed this

Eighteenth Day of November 1997

Attest:

BRUCE LEHMAN

Attesting Officer      Commissioner of Patents and Trademarks